United States Patent [19]

Delgado et al.

[11] Patent Number: 5,735,808
[45] Date of Patent: Apr. 7, 1998

[54] CONTAMINATION SAMPLING DEVICE

[75] Inventors: Felix A. Delgado, Moorpark; Susan M. Stern, Chatsworth, both of Calif.

[73] Assignee: The United States of America as represented by the Administrator of the National Aeronautics and Space Administration, Washington, D.C.

[21] Appl. No.: 687,100

[22] Filed: Jul. 10, 1996

[51] Int. Cl.⁶ ................................ A61M 35/00
[52] U.S. Cl. .................. 604/1; 128/759; 606/190; 15/210.1
[58] Field of Search ............. 604/1–3; 128/759; 606/190; 15/209.1, 210.1, 214

[56] References Cited

U.S. PATENT DOCUMENTS

| | | | |
|---|---|---|---|
| 2,668,974 | 2/1954 | Jaeger | 15/210.1 |
| 3,586,380 | 6/1971 | Alibeckoff | 604/1 |
| 3,591,885 | 7/1971 | Fritzen, Jr. | 15/210.1 |
| 3,712,296 | 1/1973 | Gradone | 128/759 |
| 4,283,809 | 8/1981 | Prost | 604/1 |

*Primary Examiner*—John G. Weiss
*Assistant Examiner*—Dennis Ruhl
*Attorney, Agent, or Firm*—Robert L. Broad, Jr.

[57] ABSTRACT

A contamination sample collection device has a wooden dowel with a cotton swab at one end, the cotton being covered by a nylon cloth and the wooden dowel being encapsulated by plastic tubing which is heat shrunk onto the dowel and onto a portion of the cotton swab to secure the cotton in place. Another plastic tube is heat shrunk onto the plastic that encapsulates the dowel and a portion of the nylon cloth to secure the nylon cloth in place. The device may thereafter be covered with aluminum foil protector. The device may be used for obtaining samples of contamination in "clean" room environments.

9 Claims, 1 Drawing Sheet

CONTAMINATION SAMPLING DEVICE

ORIGIN OF THE INVENTION

This invention was made with government support under contract NAS 8-40000 awarded by the National Aeronautics and Space Administration. The Government has certain rights in this invention.

BACKGROUND OF THE INVENTION

1. Field of the Invention

This invention relates to a sampling device for collecting contaminants from surfaces, and more particularly to a nylon covered cotton swab mounted on a wooden dowel, heat shrink tubing acting to secure the nylon in place and to secure the cotton to the dowel and to cover the handle portion of the dowel.

In a clean room environment such as in certain laboratories, production facilities and operating rooms, where sterile conditions are required, contamination by organic or inorganic substances must be avoided. It is therefore necessary to obtain samples of suspected contamination for removal from that environment and analysis of the sample at a remote site. A collection device which is precision cleaned and easy to use to obtain such samples without damaging the sampling surface is therefore a required tool for such sampling. Additionally, the collection device should be able to obtain samples in hard to reach or tight areas and obtain small contamination samples. The contamination must be able to be removed without introduction of additional contaminants which would provide inaccurate or inconsistent results. The sample to be analyzed and evaluated has to be transported from the clean room or field site to the facility where the sample is to be analyzed. In order for such a sample collecting device to be practical, it must be compatible with the fluids used for analysis and should be constructed from readily available materials so that the cost of sampling is not excessive.

Many of the requirements for such a collection device creates a number of problems. A common small, hand-held swab having a cotton tip on a wooden stem, for example, may readily be used for obtaining such samples under normal circumstances. However, cotton and wood have fibers which may be released to provide contamination on the precision cleaned surfaces to be sampled which may be overlooked or removed with great difficulty.

2. Description of Related Art

Numerous attempts to overcome such difficulties and devise a swab which provides a satisfactory solution has been proposed in the prior art. For example, in the U.S. Pat. No. 3,586,380 the cotton swab was enclosed by a thin cellulose sheath sponge. In U.S. Pat. No. 5,214,821 an absorbent tip of a tubular knit fabric, which may be monofilament polyester, nylon or polypropylene was mounted on the handle by a blind end helical wrapping. U.S. Pat. No. 3,228,398 shows a vaginal cleansing instrument comprising a polyurethane foam sponge on a plastic handle, the handle being covered by surgical tape and glued to the sponge. U.S. Pat. No. 4,192,300 discloses a swab of absorbent material impregnated with alcohol mounted on a stick and enclosed in a sealed package of foil or plastic to prevent evaporation of the alcohol. U.S. Pat. Nos. 4,635,488; 5,246,856 and 4,848,167 show specimen sampling devices used in the medical art. Although there are other swabs manufactured which may be used for contamination sampling, none of the known prior art provides a satisfactory solution to the problems heretofore described for collecting contamination samples in a clean room environment.

SUMMARY OF THE INVENTION

Consequently, it is a primary object of the present invention to provide a sampling collection device for gathering small amounts of contaminants from surfaces without itself introducing contamination so that the sample may be evaluated at a remote facility with consistent results.

It is another object of the present invention to provide a contamination sampling device constructed from readily available materials compatible with fluids used for analysis, the device being capable of obtaining samples in hard to reach areas without damage to the sampling surface and without itself introducing contamination.

It is a further object of the present invention to provide a contamination sampling device having a wooden handle with a cotton tip wherein the wood and cotton fibers are isolated from contact with the surfaces to be sampled and from the environment of a clean room.

Accordingly, the present invention provides a contamination sample collection device in the form of a swab having a wooden dowel with a cotton swab at one end, the cotton being covered by a nylon cloth and the wooden dowel being encapsulated by plastic tubing or sleeving which is heat shrunk onto the dowel and a portion of the cotton to secure the cotton, another plastic tube or sleeve being heat shrunk onto the handle and a portion of the nylon cloth to secure the nylon cloth in place. The tubing permits the dowel forming handle portion of the swab to be bent more than it otherwise could without breaking and makes it more ergonomic, and the nylon cloth may be readily cleaned. An aluminum foil covering may protect the sampling device before and after sampling.

BRIEF DESCRIPTION OF THE DRAWINGS

The particular features and advantages of the invention as well as other objects will become apparent from the following description taken in connection with the accompanying drawings in which.

DESCRIPTION OF THE PREFERRED EMBODIMENT

Figure 1:
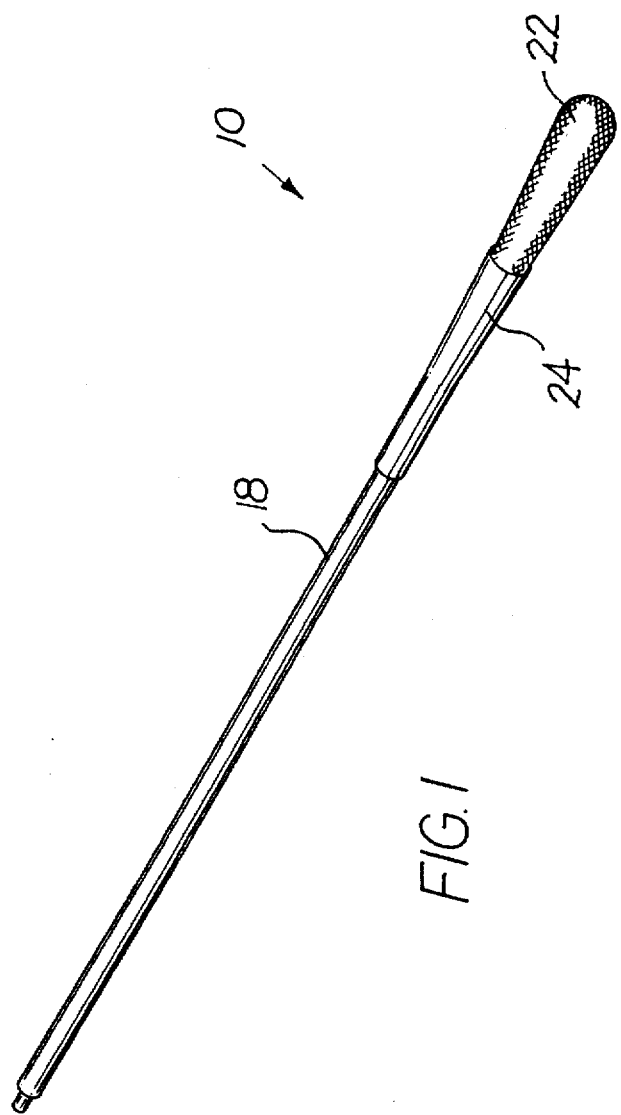
FIG. 1 is a perspective view of a contamination sample collection device constructed in accordance with the principles of the present invention.
Figure 2:
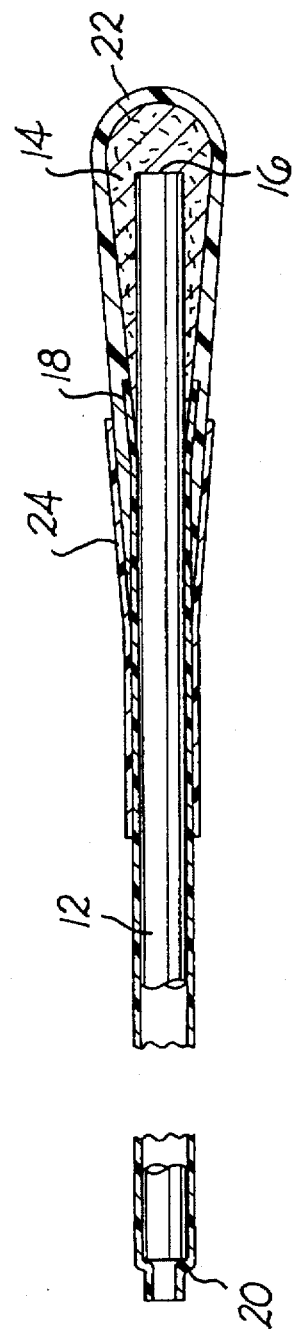
FIG. 2 is a longitudinal cross sectional view partly broken away to illustrate the details of the device illustrated in FIG. 1.

Referring to the drawings, a sampling device 10 for collecting contaminants constructed in accordance with the present invention comprises a wooden dowel 12 of approximately six inches in length and slightly less than ⅛ of an inch in diameter having a cotton mass or swab 14 wrapped about the tip 16 and a small portion adjacent thereto at the leading or working end of the dowel. No glue or similar adhesive is utilized to apply the cotton to the dowel. The cotton is, however, additionally secured to the dowel by a sheath formed from a length of synthetic plastic tubing 18 which is positioned about and receives the dowel 12 and a small end portion of the cotton swab rearwardly of the tip 16. The tubing 18 is shrinkable plastic tubing which meets the specifications of MIL-I-23053, and in a prototype the tubing was ⅛ inch inside diameter hollow tubing of approximately 5½ inches long. The tubing is then heated so that it shrinks tightly about the dowel and the small portion of the cotton wrap to secure the cotton swab to the dowel. At the tail end 20 of the dowel, i.e., the remote end from the tip, the tubing 18 is reduced in diameter substantially by heat and effectively closes the end of the dowel. The tubing 18 thus forms the handle portion of the device as a sheath over the dowel.

Disposed about the entire cotton swab 14 and over the leading end of the tubing 18 is a piece of fabric 22 formed from synthetic fiber such as nylon tricot of 40 denier, the cloth or fabric 22 being approximately two inches in diameter prior to being positioned about the cotton and tubing 18. The fabric 22 is centered over the cotton swab and is secured within the end of a piece of synthetic plastic tubing 24, which in the prototype was a piece of 3/16 inch inside diameter tubing approximately 3/4 inch long, the tubing 24 having the same specifications as the tubing 18. The tubing 24 is received over the tubing 18 from the tail end of the sampling device and the end of the fabric which extends over the tubing 18 is slid into the tubing 24. The tubing 24 is then heated to shrink it over the tubing 18 and the nylon fabric to secure the fabric over the cotton and to the handle of the device. The device is thereafter cleansed to remove any hydrocarbons to a level of less than 0.1 mg total hydrocarbons per 10 sampling devices which would otherwise interfere with subsequent use. An aluminum foil wrap may then be applied around the nylon cloth and a portion of the shaft to cover approximately two inches of the device from the tip of the leading or working end.

In use, the sampling device is removed from the protective aluminum foil and then rubbed upon the suspected contamination. Following contamination removal, the device is rewrapped in the original foil for transport to the laboratory for analysis. The suspected contamination may then be extracted and analyzed.

The encapsulation of the wooden dowel and the covering of the cotton encloses items that normally are not admissible in a clean room from the environment therein. The tubing covering the wooden dowel permits it to be bent into an overstressed condition so that the device may be used to obtain samples in hard to reach relatively inaccessible small areas. Additionally, the tubing provides a non-slip finish and a easy to hold ergonomic handle even when held by "clean" gloves which may be required during the sampling procedure.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A contamination sampling device for gathering contaminants comprising, an elongated handle having a configuration including an exterior surface and two ends, a mass of cotton positioned about and covering the surface at one end of said handle and overlaying part of said surface adjacent to said one end, a synthetic plastic sheath disposed tightly about substantially the remainder of said surface and having a leading end disposed about a portion of the exterior surface of said cotton spaced from said one end, a sheet of fabric cloth formed from synthetic fiber wrapped about the remainder of the surface of said cotton and disposed on a leading end portion of said plastic sheath, and a synthetic plastic tube overlaying and secured to at least part of said sheath and disposed tightly on the fabric spaced from said one end, whereby said fabric at said one end may collect contaminants while said device is held by said sheath remote from said one end.

2. A contamination sampling device as recited in claim 1, wherein said sheath comprises heat shrinkable plastic tubing.

3. A contamination sampling device as recited in claim 1, wherein said synthetic fiber comprises nylon.

4. A contamination sampling device as recited in claim 1, wherein said tube comprises heat shrinkable plastic.

5. A contamination sampling device as recited in claim 1, wherein said handle comprises wood.

6. A contamination sampling device as recited in claim 5, wherein said synthetic fiber comprises nylon.

7. A contamination sampling device as recited in claim 6, wherein said sheath comprises heat shrinkable plastic tubing.

8. A contamination sampling device as recited in claim 7, wherein said tube comprises heat shrinkable plastic.

9. A contamination sampling device for gathering contaminants comprising, an elongated wooden cylindrical dowel having two ends, a swab of cotton covering one end extending toward said second end, a first tube of heat shrinkable plastic disposed on said dowel and shrunk onto a portion of said cotton to secure said cotton in place, a piece of nylon cloth covering said cotton and a portion of said first tube of plastic, and a second tube of heat shrinkable plastic disposed over said first tube of plastic and shrunk onto a portion of said cloth to secure said cloth to said cotton and to said first tube.

* * * * *